United States Patent [19]

Hammar et al.

[11] 4,246,179

[45] Jan. 20, 1981

[54] CERTAIN BENZOFURAN BENZENE ACETIC ACID TYPE COMPOUNDS

[75] Inventors: Walton J. Hammar; Mark A. Rustad, both of St. Paul, Minn.

[73] Assignee: Riker Laboratories, Inc., Northridge, Calif.

[21] Appl. No.: 113,531

[22] Filed: Jan. 21, 1980

Related U.S. Application Data

[62] Division of Ser. No. 13,543, Feb. 21, 1979, Pat. No. 4,208,337, which is a division of Ser. No. 862,014, Dec. 19, 1977, Pat. No. 4,153,721.

[51] Int. Cl.³ .................. C07D 307/79; C07D 307/85
[52] U.S. Cl. ................................................. 260/346.22
[58] Field of Search ..................................... 260/346.22

[56] References Cited

U.S. PATENT DOCUMENTS

| 3,682,976 | 8/1972 | Kaltenbronn et al. | 260/346.22 |
| 3,862,134 | 1/1975 | Scherrer | 260/346.22 |
| 4,048,323 | 9/1977 | Scherrer | 260/346.22 |
| 4,066,782 | 1/1978 | Scherrer | 260/346.22 |
| 4,067,993 | 1/1978 | Scherrer | 424/285 |
| 4,124,704 | 11/1978 | Scherrer | 424/180 |

Primary Examiner—Henry R. Jiles
Assistant Examiner—Bernard Dentz
Attorney, Agent, or Firm—Cruzan Alexander; Donald M. Sell; Donald C. Gipple

[57] ABSTRACT

Compounds wherein 2-nitrobenzofuran is substituted by one or two phenyl groups and certain other substituents which are active as antimicrobial agents, processes for their use and intermediates therefor.

4 Claims, No Drawings

CERTAIN BENZOFURAN BENZENE ACETIC ACID TYPE COMPOUNDS

This is a division of copending application Ser. No. 13,543 filed Feb. 21, 1979 now U.S. Pat. No. 4,208,337, Ser. No. 13,543 being a division of copending application Ser. No. 862,014 filed Dec. 19, 1977, now U.S. Pat. No. 4,153,721.

BACKGROUND OF THE INVENTION

This invention relates to a class of 2-nitrobenzofuran derivatives wherein the 3-position is substituted by a methyl, ethyl or phenyl group, the benzo ring is substituted by a phenyl group, and one additional substituent selected from carboxyl, hydroxymethyl, hydroxyethyl, carboxymethyl and ureidomethyl is present, and pharmaceutically acceptable salts of the acids. It also relates to the use of the compounds as antimicrobial agents and to synthetic intermediates useful for the preparation of the compounds of the invention.

Compounds wherein 2-nitro-3-phenylbenzofuran is substituted by a carboxyl group or an alkanoic acid group are known to have antimicrobial activity (see Belgian Pat. No. 846,502 and German Offenlegungsschrift No. P 2642877). The compounds of the present invention which contain such groups differ from these prior art compounds in that they additionally have a phenyl group bonded to the benzo ring. The prior art does not disclose compounds which are structurally similar to the remaining compounds of the invention (i.e. which do not contain a carboxyl group or an alkanoic acid group).

DETAILED DESCRIPTION OF THE INVENTION

The present invention relates to 3-substituted-(4,5,6 or 7-phenyl)-2-nitrobenzofurans substituted by carboxy (—COOH), carboxymethyl (—CH₂COOH), hydroxymethyl (—CH₂OH), hydroxyethyl (—CH₂CH₂OH) or ureidomethyl

(—CH₂NHCNH₂)

groups and to chlorides and simple alkyl esters and salts of the acids. It also relates to use of the compounds as antimicrobial agents and to synthetic intermediates useful for the preparation of the compounds of the invention.

According to the present invention there is provided a class of compounds of the formula

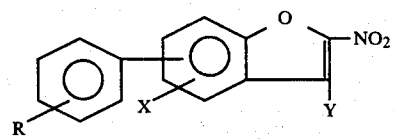

wherein
R is hydrogen, carboxyl, carboxymethyl, hydroxymethyl, hydroxyethyl or ureidomethyl,
X is hydrogen or carboxyl and
Y is methyl, ethyl, phenyl or carboxyphenyl
provided that the compound contains one and only one group selected from carboxyl, carboxymethyl, hydroxymethyl, hydroxyethyl or ureidomethyl and provided further that when R is carboxymethyl, Y is methyl or ethyl, and, when an acid group is present, acid chlorides, lower alkyl esters and pharmaceutically acceptable salts thereof (in which the lower alkyl group of the ester contains one to four carbon atoms).

The compounds of the invention are ordinarily white or yellow solids when purified. They are substantially insoluble in water or aliphatic hydrocarbons, and are more soluble in lower alcohols, halogenated solvents, benzene, N,N-dimethylformamide and the like. The alkali metal salts of acids of the invention have appreciable solubility in water and lower alkanols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animal tests. For applications in which water solubility is of importance, the salts of acids of the invention may be used.

The compounds of the invention in which X is hydrogen form a preferred subclass. Another preferred subclass is comprised of the compounds of the invention in which Y is phenyl. The alkali metal, alkaline earth, aluminum, iron and other metal and amine salts are often the equivalents of the corresponding acid-form compounds, and offer advantages in solubility, absorption, persistence, formulation and the like. The salts are of particular interest for topical uses (e.g. ophthalmic and dermatologic). The alkali metal salts (e.g. sodium and potassium) are preferred.

The final compounds of the invention are prepared by several methods (often requiring multiple-step reactions). Thus, the compounds wherein Y is carboxyphenyl (and X and R are therefore necessarily hydrogen) or wherein one of X and R is carboxyl (and Y is necessarily phenyl and the other of X and R is necessarily hydrogen) are prepared by starting with an α-bromoacetophenone and a hydroxybiphenyl according to the following reaction scheme:

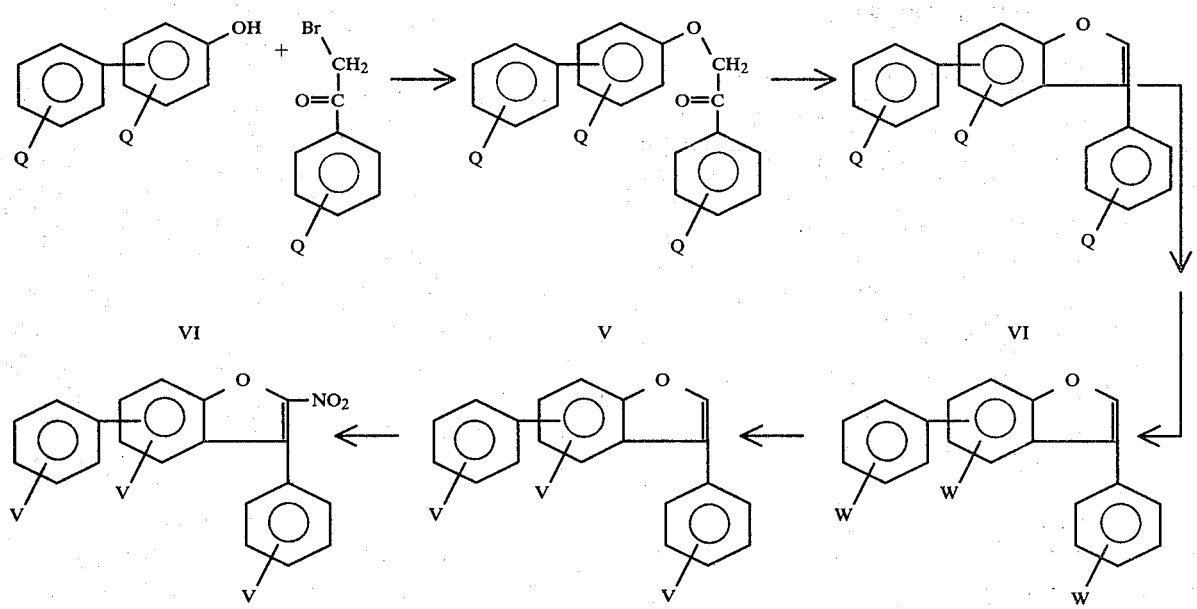

wherein one of the Q groups in each compound II–III is bromine and two are hydrogen, one of the W groups in IV is cyano and two are hydrogen, and one of the V groups in each compound V and VI is carboxyl and two are hydrogen.

The reaction to prepare the novel intermediate condensation products of formula II is generally carried out at reflux in an inert solvent such as benzene, acetone and the like and in the presence of a weak base such as sodium or potassium carbonate. Increased basicity may be used to increase the rate of reaction, if desired. The condensates II are cyclized by heating in the presence of polyphosphoric acid to form the compounds III which are, in turn, reacted with a metal cyanide, preferably cuprous cyanide, in a basic organic solvent such as pyridine or quinoline at elevated temperatures of 100°–250° C. to form the products IV. These are converted to the corresponding carboxylic acids V by hydrolysis under basic or acidic conditions.

The compounds of formula V are converted to the desired 2-nitro compounds of formula VI (which fall within the class of compounds covered by formula I) either by direct nitration or by halogen displacement (i.e. specifically halogenating the 2-position of the benzofuran group of the compound V, then replacing the 2-halogen atom with a nitro group employing a nitrating reagent).

The direct nitration can be carried out with fuming nitric acid in acetic acid or acetic anhydride or with dinitrogen tetraoxide in an inert solvent such as dichloromethane. In order to avoid aromatic nitration moderate temperatures of 0° to 30° C. are generally used.

The halogenation step of the second process may be bromination or iodination. The bromation can be carried out using N-bromosuccinimide or preferably bromine in a suitable solvent such as dichloromethane or acetic acid. Bromination is carried out under mild conditions, e.g. 0° to 30° C. to avoid aromatic bromination. The bromo compound may be isolated or used without isolation. Isolation may be carried out by extraction, precipitation by the addition of a non-solvent such as water, evaporation of volatile reaction components, etc. The iodination is carried out e.g. with a molecular iodine in the presence of yellow mercuric oxide in an inert solvent such as benzene. Generally these reactions are carried out at about 25° to 125° C., for example at the reflux temperature of the solvent.

In the final step of the halogen displacement process, the 2-halo substituent can be displaced by means of selective nitrating agents, such as strong nitric acid solution, for example 70 percent aqueous nitric acid, dinitrogen tetraoxide in e.g. acetic acid or dichloromethane solution or a mixture of sodium nitrite and a strong acid. When 70 percent nitric acid is used as the nitrating reagent for 2-halo derivatives, preferably about two or three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml. per gram required), and concentrated sulfuric acid is added, from two to ten milliliters per gram of benzofuran. Sodium nitrite is then added to the solution. The reaction temperature is about 20° to 100° C., and preferably about 55° C. The sodium nitrite can be replaced in this reaction by other metal nitrites such as potassium nitrite. In each of the preceding nitration methods, polynitration is a side-reaction.

A combination of dinitrogen tetraoxide in an inert solvent in the presence of an alkene is one presently preferred nitration method according to the halogen displacement process, with acetic acid and dichloromethane as the preferred solvents. For example, two to five liters of acetic acid per mole of benzofuran or halobenzofuran derivatives are generally used. At least one mole of dinitrogen tetraoxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of $BrNO_2$ and minimize bromination as a side reaction. Cyclohexene is satisfactory for this use. Preferably equimolar amounts of alkene and dinitrogen tetraoxide are used. The olefin is chosen to be less reactive to $N_2O_4$ than the benzofuran but more reactive to $BrNO_2$ than the benzofuran. An acidic olefin, e.g. 3-cyclohexene carboxylic acid, is advantageous when the nitrated product is neutral. The temperature of these reactions is generally about 0° to 80° C., preferably 20° to 45° C. for bromine exchange and about 0° to 25° C. for iodine exchange and direct nitration. When 2-iodobenzofurans are used, the olefin is not required (since the iodine is generally unreactive to the benzofuran under the reaction conditions) and only one-half mole of $N_2O_4$ is theoretically then required.

The compounds of formula I in which R is hydroxymethyl or hydroxyethyl are prepared by reduction of the corresponding carboxylic acids or acetic acids or their esters. The preparation of the carboxylic acids and the acetic acids, except for those acetic acids in which Y is phenyl or substituted phenyl, are described elsewhere herein. The acetic acid intermediates in which Y is phenyl or substituted phenyl are prepared as follows:

(Hydroxyphenyl)phenylacetic acids are reacted by known methods with optionally substituted α-bromoacetophenones to provide compounds of the formula

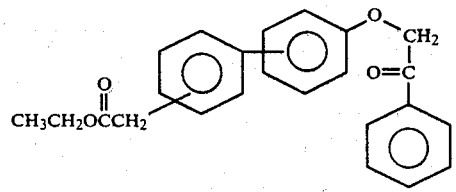

These compounds are cyclized by heating at about 50° to 100° C. in polyphosphoric acid. Simple basic hydrolysis of the esters provides compounds of the formula

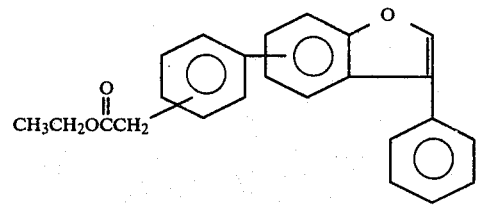

which are the desired acetic acid intermediates.

The reductions to prepare the hydroxymethyl and hydroxyethyl compounds of the present invention are carried out using hydride reducing agents such as sodium borohydride, lithium aluminum hydride or borane. The reductions can be carried out on suitable reactants either before or after the benzofuran ring has been substituted by the 2-nitro group. Such reactions are carried out in suitable non-reactive solvents known to those skilled in the art such as diethyl ether, toluene, tetrahydrofuran and the like. Reaction temperatures are generally up to the reflux temperature of the reaction solvent. Cooling may be necessary to maintain control of the rate of reaction.

The compounds of the invention wherein R is a ureidomethyl group are prepared in several steps from the corresponding acetic acid-substituted compounds. The acids are first converted to the corresponding acid chlorides by conventional methods, such as reaction with thionyl chloride or oxalyl chloride, followed by reaction with sodium azide and conversion to the isocyanate by heating in toluene. Finally, the isocyanate is reacted with ammonia or the appropriate amines to provide the ureidomethyl-substituted or the N-substituted or N,N-disubstituted ureidomethyl-substituted compounds.

The latter reaction is carried out in an inert solvent such as dichloromethane, preferably at temperatures of −20° to 30° C. to maintain control of the reaction. If it is necessary to increase the reaction rate, temperatures up to the reflux temperature of the reaction mixture are used.

Compounds of the invention wherein R is —CH$_2$CO$_2$H and Y is methyl or ethyl are prepared starting with the corresponding (hydroxyphenyl)phenylacetic acid and α-halomethyl methyl ketone, α-halomethyl ethyl ketone or e.g. α-chloroacetoacetate followed by hydrolysis and decarboxylation according to the following reaction scheme:

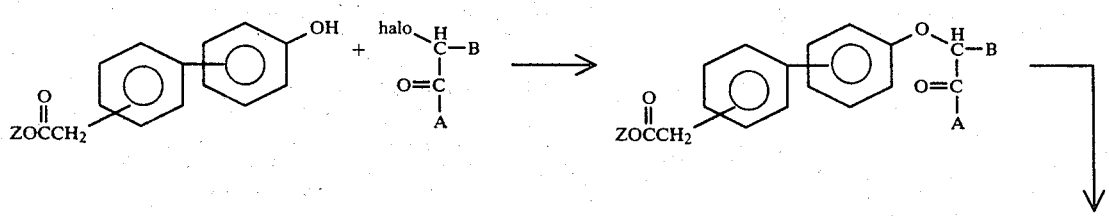

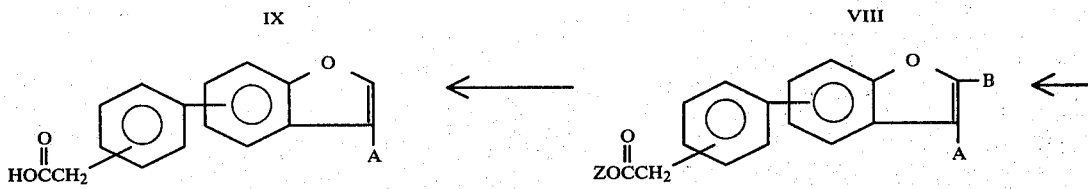

wherein Z is hydrogen or alkyl of one to four carbon atoms, A is methyl or ethyl and B is hydrogen or ethyl carboxylate. The intermediate compounds VII, VIII and IX are novel and form separate aspects of the present invention. The reaction to form the compounds VII is generally run at reflux, in an inert solvent in the presence of a base such as sodium carbonate or, when ethyl α-chloroacetoacetate is used, the preferred base is sodium ethoxide.

The cyclization in polyphosphoric acid or sulfuric acid of compounds of formula VII gives compounds of formula VIII. When B is ethyl carboxylate, hydrolysis and decarboxylation give compounds of the formula IX (wherein B and Z are hydrogen).

The compounds IX are converted to the corresponding 2-nitro compounds of formula I either by direct nitration or by preparing the corresponding 2-halo compound then replacing the halogen with a nitro group employing a nitrating agent, as previously described. The novel intermediate 2-iodo and 2-bromo compounds, which are also novel, are prepared by iodination (e.g. in the presence of mercuric oxide) or bromination, both in an inert solvent.

The pharmaceutically acceptable salts of the invention are readily prepared by reaction of the corresponding free acids with the appropriate base and optionally in a suitable solvent and evaporation to dryness. The base used to prepare the salts may be organic, e.g. sodium methoxide or an amine, or inorganic. Furthermore, other salts which are not pharmaceutically acceptable may be useful for the synthesis of the acid compounds or other, acceptable salts.

The acid chlorides and simply alkyl esters of the acid compounds of the invention are prepared starting, for example, with the corresponding acids. Thus, the acid chlorides may be made by reaction of the acids with thionyl chloride, oxalyl chloride and the like, and the esters by reaction of the acid chlorides with a lower alkanol.

The antimicrobial activity of the compounds is evaluated using a variation of the original agar-plate diffusion method of Vincent and Vincent (e.g. see Vincent, J. G., and Vincent, Helen W., Proc. oc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli,* Streptococcus sp. (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The invivo antimicrobial activity is determined against infections produced by *Streptococcus pyogenes* C-203 and *Staphylococcus aureus* (Smith) or other bacterial species. The species used is determined by the in vitro antimicrobial spectrum of the compound. Groups of five or ten mice, 18–22 g., are infected intraperitoneally with the test culture. Treatment consists of three oral injections one, six and 24 hours after infection. All mice are observed for extended periods, e.g. for two weeks, and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for treatment of a microbial infection will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids or antibacterial agents, or to combine more than one compound described herein in a single composition.

Certain of the compounds are also active antiparasitics as shown by activity in laboratory tests versus the protozoan Trichomonas sp. In view of the outstanding antimicrobial activity of the compounds, they would also be expected to be effective growth promoters in various animals and bird species.

The following examples are given for the purpose of illustrating the procedures useful for preparing compounds of the invention, but are not intended to limit the scope of the invention. The melting points are uncorrected, and the temperatures are in degrees Centigrade.

EXAMPLE 1

Step A.

A mixture of 10 g. (0.039 mole) of ethyl 4-(4-hydroxyphenyl)phenylacetate, 7.8 g. (0.039 mole) of α-bromoacetophenone and 11 g. (0.8 mole) of potassium carbonate in 250 ml. of benzene is heated at its reflux temperature for about six days. The mixture is washed with water, twice with 100 ml. of 10 percent sodium hydroxide, then 100 ml. of 6 N hydrochloric acid and dried over calcium sulfate. The solvent is evaporated to provide a residue which is triturated with hexane. Recrystallization of the solid product from an ethyl acetate-hexane mixture provides α-4-[4-(carboethoxymethyl)phenoxy]acetophenone. Structural assignment is confirmed by infrared and nuclear magnetic resonance spectral analysis.

Step B.

A mixture of 5.9 g. of acetophenone product from step A and 60 g. of polyphosphoric acid is heated at 70° to 80° C. for 1.5 hours. Thin layer chromatographic analysis indicates reaction is complete. The mixture is poured in 600 ml. of water and stirred, then extracted with chloroform. The extracts are dried over magnesium sulfate, then evaporated to provide 3-phenyl-5-[(4-carboethoxymethyl)phenyl]benzofuran. Structural assignment is confirmed by infrared and nuclear magnetic resonance spectral analysis.

Step C.

A mixture of the benzofuran product from step B, 50 ml. of 10 percent sodium hydroxide solution and 100 ml. of ethanol is heated on a steam bath for two hours. The ethanol is evaporated and the residual solution is acidified with 6 N hydrochloric acid. The product gradually crystallizes and is recrystallized from aqueous ethanol to give 3-phenyl-5-[(4-carboxymethyl)phenyl]benzofuran. Structural assignment is confirmed by infrared and nuclear magnetic resonance spectral analysis.

Step D.

A solution of 3.1 g. of 3-phenyl-5-[(4-carboxymethyl)phenyl]benzofuran and 2 g. of dinitrogen tetraoxide in 200 ml. of dichloromethane is stirred for about 16 hours at about 20° C. The solvent is evaporated, and the residue is eluted from silica gel with chloroform. The product is obtained as a yellow solid and recrystallized from a benzene-hexane mixture to provide 2-nitro-3-phenyl-5-[(4-carboxymethyl)phenyl]benzofuran, m.p. 194°–197° C. This compound can also be named as 4-(2-nitro-3-phenylbenzofuran-5-yl)phenylacetic acid.

| Analysis: | % C | % H | % N |
| --- | --- | --- | --- |
| Calculated for $C_{22}H_{15}NO_5$: | 70.8; | 4.0; | 3.7 |
| Found: | 70.1; | 3.9; | 3.8. |

Step E.

To a solution of 4 g. (0.0106 mole) of 4-(2-nitro-3-phenylbenzofuran-5-yl)phenylacetic acid in 200 ml. of benzene at 5° C. is added slowly 4.1 g. (0.032 mole) of oxalyl chloride in 10 ml. of benzene. The reaction is stirred for 30 minutes while warming to about 20° C., then heated at reflux for three hours. Evaporation to dryness provides a residue which forms yellow solid 4-(2-nitro-3-phenylbenzofuran-5-yl)phenylacetyl chloride when triturated with a hexane-benzene mixture.

Step F.

To a solution of 2 g. (0.0051 mole) of sodium azide in 5 ml. of water and 5 ml. of acetone at 5° C. is slowly added the product of step E in 50 ml. of acetone. Stirring is continued for two hours, after which the mixture is poured into 300 ml. of ice water. The solution is extracted thrice with 200 ml. portions of toluene. The toluene layers are dried, then heated at reflux for four hours. Evaporation provides 4-(2-nitro-3-phenylbenzofuran-5-yl)phenylmethyl isocyanate.

Step G.

The residue from Step F is dissolved in 100 ml. of dichloromethane, the solution is cooled to 5° C. and ammonia is bubbled in for 10 minutes. Cooling provides a yellow solid which is separated by filtration to provide 3-phenyl-5-[4-(ureidomethyl)phenyl]-2-nitrobenzofuran, m.p. 215°–216° C.

| Analysis: | % C | % H | % N |
| --- | --- | --- | --- |
| Calculated for $C_{22}H_{17}N_3O_4$: | 68.2; | 4.4; | 10.8 |
| Found: | 68.1; | 4.5; | 10.8. |

EXAMPLE 2

A solution of 2 g. (0.00536 mole) of 4-(2-nitro-3-phenylbenzofuran-5-yl)phenylacetic acid (the product of step D of Example 1 hereof) in 100 ml. of tetrahydrofuran is cooled to 0° C. and 20 ml. of a borane solution in tetrahydrofuran is added while under a nitrogen atmosphere over 10 minutes. After warming to 20° C. the mixture is stirred for 16 hours. The solution is cooled to 0° C., 50 ml. of 1:1 water-tetrahydrofuran mixture and 15 ml. of 3 N sulfuric acid are each added slowly and the mixture is stirred at 20° C. for 45 minutes. Evaporation provides a residue which crystallizes when triturated with hexane. Chromatography through silica gel in chloroform, eluting with chloroform, provides 5-[4-(2-hydroxyethyl)phenyl]-2-nitro-3-phenylbenzofuran, m.p. 86°–87° C.

| Analysis: | % C | % H | % N |
| --- | --- | --- | --- |
| Calculated for $C_{23}H_{17}NO_4$: | 73.5; | 4.77; | 3.9 |
| Found: | 73.9; | 5.1; | 3.5. |

EXAMPLE 3

Step A.

A mixture of 137 g. (0.55 mole) of 2-bromo-4-phenylphenol, 109 g. (0.55 mole) of α-bromoacetophenone and 75 g. of sodium carbonate in 1.5 liters of acetone is heated at its reflux temperature for six days, filtered, then evaporated. The white residue is recrystallized from a benzene-hexane mixture to provide white needles of α-(2-bromo-4-phenylphenoxy)acetophenone, m.p. 93°–95° C.

Step B.

A mixture of 156 g. of the product of step A and 1 kg. of polyphosphoric acid is heated at 100° C. for seven days. The reaction mixture is poured into 5 liters of water and stirred, then extracted with 2 liters of chloroform. The dried extracts are treated with decolorizing charcoal, then evaporated. The residue is chromatographed on silica gel, eluting with carbon tetrachloride. The residue is triturated with hexane to provide 7-bromo-3,5-diphenylbenzofuran as a pale yellow solid. The structural assignment is supported by infrared and nuclear magnetic resonance spectral analysis.

Step C.

A mixture of 64 g. (0.18 mole) of the product of step B, 17.8 g. (0.2 mole) of cuprous cyanide and 35 ml. of pyridine is heated under a nitrogen atmosphere at 150° to 160° C. for one day. The mixture is poured into 1 liter of 3 N hydrochloric acid, extracted with 1 liter of dichloromethane, and the extracts are dried. Evaporation provides a residue which is chromatographed on silica gel, eluting with dichloromethane, to provide 7-cyano-3,5-diphenylbenzofuran as a pale yellow solid. The structural assignment is supported by infrared and nuclear magnetic resonance spectral analysis.

Step D.

A mixture containing 30 g. (0.10 mole) of the product of step C, 14.5 g. (0.22 mole) of 85 percent potassium hydroxide, 400 ml. of ethanol and 50 ml. of water is heated at its reflux temperature for 16 hours, cooled and filtered. The product is washed with ethanol, suspended in water and acidified with 6 N hydrochloric acid. The mixture is heated on a steam bath for one hour, cooled and filtered. Recrystallization from ethanol provides 3,5-diphenylbenzofuran-7-carboxylic acid as a white solid.

Step E.

A solution of 4.0 g. (0.013 mole) of the product of step D in 50 ml. of dioxane is treated with 2.4 g. of bromine in 450 ml. of chloroform, and the mixture is heated at its reflux temperature overnight. The solution is cooled, washed with water, dried and then evaporated. The residue is triturated with hexane to provide 2-bromo-3,5-diphenylbenzofuran-7-carboxylic acid as a white solid, m.p. 232°–236° C.

Step F.

A solution of 6 g. (0.018 mole) of the product of step E in hot acetic acid is treated with 6 ml. of 70 percent nitric acid while the solution is maintained at about 80° C. Sodium nitrite (2.7 g., 2 equivalents) is added gradually, and the mixture is heated on a steam bath for 45 minutes. The mixture is then poured into 500 ml. of water. The solid is filtered, recrystallized twice from acetone, then from an ethyl acetate-hexane mixture to provide yellow crystals of 3,5-diphenyl-2-nitrobenzofuran-7-carboxylic acid, m.p. 207°–209° C.

| Analysis: | % C | % H | % N |
|---|---|---|---|
| Calculated for $C_{21}H_{13}NO_5$: | 70.2; | 3.6; | 3.9 |
| Found: | 69.8; | 3.6; | 3.7. |

EXAMPLE 4

Step A.

A mixture of 71.7 g. (0.40 mole) of 4-(4-bromophenyl)phenol, 79.1 g. (0.40 mole) of α-bromoacetophenone and 74 g. (0.7 mole) of sodium carbonate in one liter of acetone is heated at its reflux temperature for three days. Filtration and evaporation provides a residue which is triturated with hexane, filtered and recrystallized from ethanol. The product is white needles of α-[4-(4-bromophenyl)phenoxy]acetophenone. Its structural assignment is supported by infrared and nuclear magnetic resonance spectral analysis.

Step B.

A mixture of 72 g. of the product of step A and 700 g. of polyphosphoric acid is heated at 100° C. for three days, poured into 1.5 liters of water and stirred. The mixture is extracted with chloroform (1 liter), the extracts dried, then evaporated. The residue is dissolved in benzene, and hexane is added to precipitate white solid which is removed by filtration. The filtrate is evaporated and the residue triturated with hexane to provide 5-(4-bromophenyl)-3-phenylbenzofuran.

Step C.

A mixture of 21 g. of the product of step B, 12 g. of cuprous cyanide and 25 ml. of pyridine is heated at 150°–160° C. under a nitrogen atmosphere for 24 hours, then poured into 200 ml. of 3 N hydrochloric acid and stirred. Dichloromethane (150 ml.) is added, the mixture is filtered, the organic layer is separated, washed with water and dried. Evaporation provides a residue which is purified by eluting through a silica gel column with carbon tetrachloride to provide, after evaporation of the solvent, 5-(4-cyanophenyl)-3-phenylbenzofuran.

Step D.

A mixture of 10.2 g. (0.034 mole) of the product of step C, 3.6 g. (0.068 mole) of 85 percent potassium hydroxide, 20 ml. of water and 200 ml. of ethanol is heated at its reflux temperature for three days, evaporated, then acidified with 6 N hydrochloric acid. The solid obtained is recrystallized from benzene to provide 4-(3-phenylbenzofuran-5-yl)benzoic acid as a white solid. The structural assignment is supported by infrared and nuclear magnetic resonance analysis.

Step E.

A solution of 3.1 g. (0.01 mole) of the product of step D and 2 g. of dinitrogen tetraoxide in 250 ml. of chloroform is stirred at about 20° C. for about 16 hours. Evaporation of the mixture provides a residue which is dissolved in 10 percent sodium hydroxide solution, then acidified with hydrochloric acid. The precipitate is collected by filtration, dissolved in a chloroform/ethanol mixture and chromatographed on silica gel, eluting with chloroform. The solid obtained is recrystallized twice from a mixture of water and N,N-dimethylformamide to provide yellow crystals of 4-(2-nitro-3-phenylbenzofuran-5-yl)benzoic acid, m.p. 259°–261° C.

| Analysis: | % C | % H | % N |
|---|---|---|---|
| Calculated for $C_{21}H_{13}NO_5$: | 70.2; | 3.6; | 3.9 |
| Found: | 69.9; | 3.8; | 4.0. |

EXAMPLE 5

Step A.

A solution of 75 g. (0.441 mole) of 4-hydroxybiphenyl, 50 g. of sodium carbonate and 100 g. (0.36 mole) of α-bromo-4'-bromoacetophenone is heated at its reflux temperature for about 6 hours, stirred at 20° C. for one day, diluted with 500 ml. of acetone and filtered hot. After cooling, the solid is collected by filtration to provide α-(4'-phenylphenoxy)-4-bromoacetophenone, m.p. 131°–133° C.

| Analysis: | % C | % H |
|---|---|---|
| Calculated for $C_{20}H_{15}BrO_2$: | 65.4; | 4.1 |
| Found: | 65.9; | 4.2. |

Step B.

A mixture of 86.3 g. of the product of step A and 800 g. of polyphosphoric acid is heated at 120° C. for about 18.5 hours, poured into ice water, then extracted with diethyl ether. The extracts are washed with saturated sodium chloride solution and dried. The solid obtained is recrystallized from hexane to provide 3-(4-bromophenyl)-5-phenylbenzofuran, m.p. 90°–92° C.

| Analysis: | % C | % H |
|---|---|---|
| Calculated for $C_{20}H_{13}BrO$: | 68.8; | 3.4 |
| Found: | 68.8; | 3.6. |

Step C.

A mixture of 58 g. of the product of step B, 17 g. of cuprous cyanide and 14 ml. of pyridine is heated at 200° C. for about four hours, then poured into 50 g. of ferric chloride, 60 ml. of 6 N hydrochloric acid and ice. Extraction with diethyl ether is followed by washing of the extracts with saturated sodium chloride solution and drying. Evaporation gives a residue which is chromatographed on silica gel, eluting with carbon tetrachloride, then a dichloromethane-carbon tetrachloride mixture to provide 3-(4-cyanophenyl)-5-phenylbenzofuran.

Step D.

A mixture of 25.1 g. of the product of Step C, 8.0 g. of sodium hydroxide, 40 ml. of water and 40 ml. of ethanol is heated at its reflux temperature for 16 hours, acidified and the solid collected by filtration. Recrystallization from aqueous ethanol provides 4-(5-phenylbenzofuran-3-yl)benzoic acid, m.p. 245°–248° C.

| Analysis: | % C | % H |
|---|---|---|
| Calculated for $C_{21}H_{14}O_3$: | 80.2; | 4.5 |
| Found: | 80.1; | 4.5. |

Step E.

A mixture of 3.2 g. of the product of step D, 2 g. of dinitrogen tetraoxide, 1 ml. of acetic acid and 200 ml. of dichloromethane is stirred at 20° C. for 16 hours, washed with water and evaporated. The residue is treated with cold 5 percent sodium hydroxide solution, then acidified with 6 N hydrochloric acid. The solid residue is separated and recrystallized from N,N-dimethylformamide to provide 4-(2-nitro-5-phenylbenzofuran-5-yl)benzoic acid, m.p. 235°–249° C.

| Analysis: | % C | % H | % N |
|---|---|---|---|
| Calculated for $C_{21}H_{13}NO_5$: | 70.2; | 3.6; | 3.9 |
| Found: | 70.1; | 3.6; | 3.7. |

EXAMPLE 6

Step A.

To a solution of 0.25 mole of sodium ethoxide is added 64 g. (0.25 mole) of ethyl 4-(4-hydroxyphenyl)-phenylacetate. After stirring two hours the solution is evaporated, benzene is added, and the solution is further evaporated. The residue is dissolved in 800 ml. of benzene, 0.25 mole of ethyl α-chloroacetoacetate is added, and the mixture is stirred at room temperature, then heated at its reflux temperature for 16 hours and filtered hot. Evaporation provides a residue which is dissolved in carbon tetrachloride and filtered through silica gel. This intermediate is treated with concentrated sulfuric acid at 0° C. After stirring one hour, ice is added and the mixture is extracted with benzene. The benzene layer is dried, then evaporated. The residue is recrystallized from a dichloromethanehexane mixture, then carbon tetrachloride, to provide ethyl 4-(2-ethoxycarbonyl 3-methylbenzofuran-5-yl)phenylacetate, m.p. 110°–112° C.

| Analysis: | % C | % H |
|---|---|---|
| Calculated for $C_{22}H_{22}O_5$: | 72.1; | 6.05 |
| Found: | 72.1; | 6.1. |

Step B.

A solution of 17 g. of the product of step A in 100 ml. of acetic acid with 35 ml. of 48 percent hydrobromic acid is heated at reflux for three hours, then poured into ice water. This mixture is extracted into dichloromethane, and the extracts are dried to provide 4-(3-methylbenzofuran-5-yl)phenylacetic acid. This intermediate is esterified by heating with a trace of sulfuric acid in ethanol. The product is purified by chromatography on silica gel, eluting with 20 percent dichloromethane in carbon tetrachloride to provide ethyl 4-(3-methylbenzofuran-5-yl)phenylacetate.

Step C.

To a solution of 2.8 g. of the product of step B in 50 ml. of benzene is added 2.7 g. of iodine and 2.4 g. of mercuric oxide followed by stirring and heating at 60°–65° C. for about three days. The mixture is cooled and evaporated, and the residue is chromatographed on silica gel, eluting with a carbon tetrachloride-dichloromethane mixture, to provide ethyl 4-(2-iodo-3-methylbenzofuran-5-yl)phenylacetate. To this intermediate is added dichloromethane, then dinitrogen tetraoxide. After one hour the mixture is washed with water, then with sodium bisulfite solution and dried. Evaporation provides a residue which is recrystallized from a dichloromethane-hexane mixture to yield ethyl 4-(3-methyl-2-nitrobenzofuran-5-yl)phenylacetate.

Step D.

A solution of 1.5 g. of the product of step C in 25 ml. of acetic acid and 10 ml. of 6 N hydrochloric acid is heated at its reflux temperature for 45 minutes then poured into ice water. The precipitate is collected and recrystallized from an ethanol-N,N-dimethylformamide mixture to provide 4-(3-methyl-2-nitrobenzofuran-5-yl)phenylacetic acid, m.p. 229°–230° C.

| Analysis: | % C | % H | % N |
|---|---|---|---|
| Calculated for $C_{17}H_{13}NO_5$: | 65.6; | 4.2; | 4.5 |
| Found: | 65.9; | 4.2; | 4.6. |

What is claimed is:
1. A compound of the formula
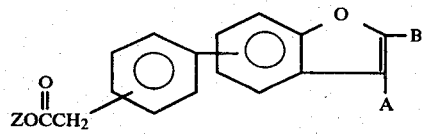
wherein Z is hydrogen or alkyl of one to four carbon atoms, A is methyl or ethyl and B is hydrogen or ethyl carboxylate.
2. Ethyl 4-(2-ethoxycarbonyl-3-methylbenzofuran-5-yl)phenylacetate according to claim 1.
3. 4-(3-Methylbenzofuran-5-yl)phenylacetic acid according to claim 1.
4. Ethyl 4-(3-methylbenzofuran-5-yl)phenylacetate according to claim 1.